US005801002A

United States Patent [19]

Raz

[11] Patent Number: 5,801,002
[45] Date of Patent: Sep. 1, 1998

[54] GALACTOSIDE-BINDING-PROTEIN USEFUL IN THE DIAGNOSIS AND INHIBITION OF OF METASTASIS

[75] Inventor: Avraham Raz, West Bloomfield, Mich.

[73] Assignee: Barbara Ann Karmanos Cancer Institute, Detroit, Mich.

[21] Appl. No.: 562,311

[22] Filed: Nov. 22, 1995

Related U.S. Application Data

[63] Continuation of Ser. No. 188,225, Jan. 26, 1994, abandoned, which is a continuation-in-part of Ser. No. 681,242, Apr. 5, 1991, abandoned, which is a continuation-in-part of Ser. No. 294,249, Jan. 6, 1989, abandoned.

[51] Int. Cl.$^6$ .................... G01N 33/574; G01N 33/53
[52] U.S. Cl. .................... 435/7.23; 435/7.9; 436/64; 436/813; 436/827; 530/387.7; 530/387.9
[58] Field of Search .................... 435/7.23, 7.9; 530/387.7, 387.9; 436/64, 813, 827

[56] References Cited

PUBLICATIONS

Raz, A., et al., *Cancer Metastasis Rev.*, vol. 6, No. 3, pp. 433–452, 1987.
Fidler, I., et al., *The Cancer Bulletin*, vol. 39, No. 3, pp. 126–131, 1987.
Oda, Y., et al., *Gene*, vol. 99, pp. 279–283, 1991.
Jia et al., "Galactose–specific Lectin–Mouse (Fragment)," 263 J. Biol. Chem. 6008–11 (1988).
Raz et al., "Differential Expression of Endogenous Lectins on the Surface of Non–tumorigenic, Tumorigenic, and Metastatic Cells",Cancer Research 46, 3667–3672, Jul. 1986.
Raz et al., "Identificaton of the Metastasis–associated, Galactoside–binding Lectin as a Chimeric Gene Product with Homology to an IgE–binding Protein", Cancer Research 49, 3489–3493, Jul. 1, 1989.
Raz et al., "Expression of Two Different Endogenous Galactoside–binding Lectins Sharing Sequence Homology", Cancer Research 48, 645–649, Feb. 1, 1988.
Raz et al., "Molecular Cloning and Chromosomal Mapping of a Human Galactoside–binding Protein", Cancer Research 51, 2173–2178, Apr. 15, 1991.
Raz et al., "Monoclonal antibodies to endogenous galactose–specific tumor cell lectins", The EMBO Journal, vol. 3, No. 12, pp. 2979–2983, 1984.
Ochieng et al., "Galectin–3 Is a Novel Substrate for Human Matrix Metalloproteinases–2 and –9", Biochemistry, vol. 33, No. 47, pp. 14109–14114, 1994.
Raz et al., "Cloning and Expression of cDNA for Two Endogenous UV–2337 Fibrosarcoma Lectin Genes", Experimental Cell Research 173 (1987), 109–116.
Robertson et al., "Human IgE–Binding Protein: A Soluble Lection Exhibiting a Highly Conserved Interspecies Sequence and Differential Recognition of IgE Glycoforms.", Biochemistry 1990, 29, 8093–8100.
Jia et al., "Carbohydrate Binding Protein 35", The Journal of Biological Chemistry, vol. 263, No. 13, May 5, 1968, 6009–6011.
Hee Jong Woo et al., "The Major Non–integrin Laminin Binding Protein of Macrophages Is Identical to Carbohydrate Binding Protein 35 (Mac–2)", The Journal of Biological Chemistry, vol. 265, No. 13, May 5, 1990, pp. 7097–7099.

*Primary Examiner*—Toni R. Scheiner
*Attorney, Agent, or Firm*—Dykema Gossett PLLC

[57] ABSTRACT

Disclosed are novel polypeptides possessing part or all of the amino acid sequence or primary structural conformation and one or more of the biological properties of certain galactoside-binding-proteins with apparent molecular weights of 34,000 and 31,000. Genomic DNA, cDNA and manufactured DNA sequences coding for part or all of the sequences of amino acid residues of L-34-gal-lectin and L-31-gal-lectin are incorporated into vectors used to transform a host cell in culture. Also provided are antibodies against L-34-gal-lectin and L-31-gal-lectin and a method for inhibiting mammalian cell metastasis by treating mammalian cells in a living host with antibodies against L-34-gal-lectin or L-31-gal-lectin. A method of determining the metastatic potential of mammalian cells is also provided by which cells in vitro are contacted with antibodies against L-34-gal-lectin or L-31-gal-lectin which are labeled with a detectable probe. An elevated level of expression of L-34-gal-lectin or L-31-gal-lectin is indicative of metastatic potential.

1 Claim, 12 Drawing Sheets

```
                                        AATCCGGTCCAGCCAGTGC    -121
AGGGCAGGGATGCTGCTGCCCTGGGAGGCGGGCCCCGGGGAAAAAGTACTAGAAGCGGC     -61
CGAGCCATCGCCCAGCTCTGACAGGCTAGCGGGAGCGGAGCACTAATCAGGAAA          -10
ATGGCAGACACGTTTTCGCTTAACGATGCCTTAGCTGGCTCTGGAAACCCTCAA           60
 M  A  D  T  F  S  L  N  D  A  L  A  G  S  G  N  P  N  P  Q
 1
GGATATCCGGGTGCATGGGGAAACCAGGGAACCAGCTGGGGTACCCAGGGGCTGCCTAT    120
 G  Y  P  G  A  W  G  N  Q  G  T  S  W  G  T  Q  G  L  P  Y
21
CCTGGGGCCTATCCAGGAGGACAGGCTCCTCCAGGGCCTACCCAGGAGCTCCTCCAGGG    180
 P  G  A  Y  P  G  G  Q  A  P  P  G  P  T  Q  E  L  L  Q  G
41
PGA Y PGGAPPGAYPGQAPPG
CGATATCCAGGAGGACAGGCTCCTCCAGGGGCCTATCCAGGGCAGGCTCCTCCAGGG
 P  G  A  Y  P  G  G  A  P  P  G  A  Y  P  G  Q  A  P  P  G
GCCTATCCAGGAGGACAGGCTCCTCCAGGGGCCTATCCAGGGCAGGCTCCTCCAGGG
AYPGQAPPSAYPGSTAPGAFPG
CCTGCCCAACTGCCCCCGGAGCTTATCCTGGCTACCCAGGGTCAACTGCTCCTGGAGCCTTTCCAGGG    300
 A  Y  P  G  Q  A  P  P  S  A  Y  P  G  S  T  A  P  G  A  F  P  G
61
CCTGGCCCAACTGCTCCAGGGGCCTATCCAGGGGCTATCCAGGGGGATATCCTGGCCCT    360
 P  G  P  T  A  P  G  A  Y  P  G  S  T  A  P  G  A  F  P  G
81
CAACCTGGGGGCGCACCTGGGGCCTATCCCAGCGCTCCTGGAGGCTATCCAGCTGGCCCT
 Q  P  G  G  A  P  G  A  Y  P  S  A  P  G  G  Y  P  A  A  G  P
101
TATGGTGTCCCCGCTGGACCACTGACCGTGCCCTATGACCTGCCCCTGCCTGGAGGACTC    420
 Y  G  V  P  A  G  P  L  T  V  P  Y  D  L  P  L  P  G  G  V
121
ATGCCCCGCATGCTGATCACAATCATGGGCACAGTGAAACCCAACGCAAACAGGATTGTT    480
 M  P  R  M  L  I  T  I  M  G  T  V  K  P  N  A  N  R  I  V
141
```

Fig - 2A

```
      CTAGATTTCAGGAGAGGGAATGATGTTGCCTTCCACTTTAACCCCCGCTTCAATGAGAAC    540
161    L  D  F  R  R  G  N  D  V  A  F  H  F  N  P  R  F  N  E  N
      AACAGAAGAGTCATTGTGTGTAACACGAAGCAGGACAATAACTGGGAAGGAAGAAGAAAGA    600
181    N  R  R  V  I  V  C  N  T  K  Q  D  N  W  Q  K  E  E  R
      CAGTCAGCCTTCCCCTTTGAGAGTGGAAAATACAAGTCCTGGTTGAAGCT              660
201    Q  S  A  F  P  F  E  S  G  K  P  F  K  I  Q  V  L  V  A  A
      GACCACTTCAAGGTTGCCGGTCAACGATGCTCACCTACTGCAGTACAACCATCGGATGAAG    720
221    E  P  F  K  V  A  V  N  D  A  H  L  L  Q  Y  N  H  R  M  K
      AACCTCCGGGAAATCAGCCAGCTGGGGATCAGTGGTGACATAACCCTCACCAGCGCTAAC    780
241    N  L  R  E  I  S  Q  L  G  I  S  G  D  I  T  L  T  S  A  N
      CACGCCATGATCTAAGCCAGAAGGGGCGGCACCGAAACCGGCCCTGTGTGCCTTAGGAGT    840
261    H  A  M  I  *
      GGGAAACTTTGCATTTCTCTCCTTATCCTTCTTGTAAGACATCCATTTAATAAAGTCT      900
      CATGCTGAGAGAAAAG
```

Fig - 2B

```
                                                                  60
     GCAGCCACCGAGCGGGAAAATGGCAGACAATTTTCGCTTCCATGATGCGTTATCTGGTCT
                             M  A  D  N  F  S  L  H  D  A  D  S  G  S
                                                                  120
     GGAAACCCAAACCCTCAAGGATGGGCATGGCCTGGGGGAACGGCAACCAGCCTGGGGCAGGG
  15 G  N  P  N  P  Q  G  W  P  G  A  W  G  N  Q  P  A  G  A  G
                                                                  180
     GGCTACCCCAGGGGCTTCCTATCCCGGGCAGGCAGCCTACCCAGGGGCTTAT
  35 G  Y  P  G  A  S  Y  P  G  A  Y  P  G  Q  A  P  P  G  A  Y
                                                                  240
     CCTGGACAGGCACCTCCAGGGCGCCTACCATGAGCTTATCCCGGAGCACCT
  55 P  G  Q  A  P  P  G  A  Y  H  G  A  P  G  A  Y  P  G  A  P
                                                                  300
     GCACCTGGAGTCTACCCCAGGGCCCCCAGCCCCATCTTCTGGACAG
  75 A  P  G  V  Y  P  G  P  P  S  G  P  G  A  Y  P  S  G  Q
                                                                  360
     CCAAGTGCCCCCGGAGCCTACCCTGCCCCCTATGCCGGTGTCCTGGCCACTG
  95 P  S  A  P  G  A  Y  P  A  T  G  P  Y  G  A  P  A  G  P  L
                                                                  420
     ATTGTGCCTTATAACCTGCCTTTGCCTGGGGAGTGGTGCCTCGCATGCTGATAACAATT
 105 I  V  P  Y  N  L  P  L  P  G  G  V  V  P  R  M  L  I  T  I
```

*Fig - 6A*

```
     CTGGGCACGGTGAAGCCCAATGCAAACAGAATTGCTTTAGATTTCCAAGAGGGAATGAT      480
135  L   G   T   V   K   P   N   A   N   R   I   A   L   D   F   Q   R   G   N   D
     GTTGCCTTCCACTTTAACCCACGCTTCAATGAGAACAACAGGAGAGTCATTGTTTGCAAT      540
155  V   A   F   H   F   N   P   R   F   N   E   N   N   R   R   V   I   V   C   N
     ACAAAGCTGGATAATAACTGGGGAAGGGAAGAAAGACAGTCGGTTTTCCCATTTGAAAGT      600
175  T   K   L   D   N   N   W   G   R   E   E   R   Q   S   V   F   P   F   E   S
     GGGAAACCATTCAAAATACATGTACTGGTTGAACTGACCACTTCAAGGTTGCAGTGAAT      660
195  G   K   P   F   K   I   H   V   L   V   E   P   D   H   F   K   V   A   V   N
     GATGCTCACTTGTTGCAGTACAATCATCGGGTTAAAAAACTCAATGAAATCAGAAAACTG      720
215  D   A   H   L   L   Q   Y   N   H   R   V   K   K   L   N   E   I   R   K   L
     GGAATTTCTGGTGACATAGACCTCACCAGTGCTTCATATACCATGATAATCTGAAAAGG      780
235  G   I   S   G   D   I   D   L   T   S   A   S   Y   T   M   I   *
     GGCAGATTAAAAAAAAAAAAAGAATCTAAACCTTACATGTGTAAAGGTTTCATGTTCA      840
     CTGTGAGAGAAAATTTTTACATTCATTCAATATATCCCCCC                           878
```

Fig-6B

```
M-L    1   MADTFSLNDALAGSGNPNPQGYPGAWGNQPGAGGYPGAAYPGAYPGQAPP       50
           ||| |||| ||||||||||| ||| || • |||||| |||• ||• |||
H-L    1   MADNFSLHDALSGSGNPNPQGWPGAWGNQPAGQGLPGASYPGAYPAGTPG       50

M-L   51   GAYPGQAPPGAYPGAYPGQAPPSAYPGPTAPGAYPGPTAPGAYPGSTAPGAFPG      100
           |||•| |||||• ||||||||||  •|
H-L   51   LSWTAPPGATMEHVELIRSTC......TWSLRTQPGAYPSSGQ.........       87

M-L  101   QPGAPGAYPSAPGGYPAAGPYGVPAGPLTVPYDLPLPGGVMPRMLITIMG         150
                                  ||||| •||•||•|||||||•|||||||
H-L   88   ..........PSAPGAYPATAPMA.PAGPLIVPYNLPLPGGVVPRMLITILG      128

M-L  151   TVKPNANRIVLDFRRGNDVAFHFNPRFNENNRRVIVCNTKQDNNWGKEER         200
           |||||||||•|| •||||||||||||||||||||||||| ||||||•|||
H-L  129   TVKPNANRIALDFQRGNDVAFHFNPRFNENNRRVIVCNTKLHNNWGREER         178

M-L  201   QSAFFPFESGKPFKIQVLVEADHFKVAVNDAHLLQYNHRMKNLREISQLGI        250
           || •|||||||||||•|•|| |||•|||||||||||||||•|||• |•||
H-L  179   QSVFFPFESGKPFKIHVLVEPDHLKVAVNDAHLLQYNHRVKKLNEIRKLGI        228

M-L  251   SGDITLTSANHAMI        264
           |||| ||||  ||
H-L  229   SGDIDLTSASYTMI        242
```

*Fig - 7*

```
Eel-L14      39   A E D L A L H I N P R F D A H   53
Chicken-L14       S T H L G L H F N P R F D A H
Mouse-L14         S N N L C L H F N P R F N A H
Rat-L14           S N N L C L H F N P R F N A H
Bovine-L14        S N N L C L H F N P R F N A H
Human-L14         S N N L C L H F N P R F N A H
Mouse-L34    166  G N D V A F H F N P R F N E N   180
Human-L31    144  G N D V A F H F N P R F N E N   158
                  ▲ ▲                     ▲ ▲
```

*Fig - 8*

```
Eel-L14      54   G D Q Q A V V V N S F Q G G N   68
Chicken-L14       G D V N I I V C N S K K M E E
Mouse-L14         G D V N L I V C N T K E D G T
Rat-L14           G D A N T I V C N S K D D G T
Bovine-L14        G D A N T I V C N S K D G G A
Human-L14         G D A N T I V C N S K D G G A
Mouse-L34    181  N R R V - I V C N T K Q D N N   194
Human-L31    159  N R R V   I V C N T K L H N N   172
                  ▲ ▲ ▲ ▲             ▲
```

*Fig - 9*

```
Eel-L14      69   W G T E Q R E G G F P F K Q G E   84
Chicken-L14       W G T E Q R E T V F P F Q K G A
Mouse-L14         W G T E H R E P A F P F Q P G S
Rat-L14           W G T E Q R E T A F P F Q P G S
Bovine-L14        W G T E Q R E A V F P F Q P G S
Human-L14         W G T E Q R E A V F P F Q P G S
Mouse-L34    195  W G K E R Q S A F P F E S G K   210
Human-L31    173  W G R E R Q S V F P F E S G K   188
                          ▲   ▲ ▲     ▲ ▲
```

*Fig - 10*

```
LACTIN  15  P N P Q G W P G A W G N Q P A G Q G L P G A S Y P G A Y P G T P
            | |   |           |     |   |         |           |
L-MYC   37  P S P P T S P - P W G L G P G A G D P A P G I G P P E P W P A G G C T

LACTIN  48  - - - G - - L S W T A P P G A T M E H V E L I R S T C T W S L R T Q
                  |         |                             |         |
L-MYC   70  G T D E A E S - P W G H S K G W G R N Y H S I H R R D C M W S G F S A R

LACTIN  78  P G A Y P S S C Q P S A P G A Y P A T A P M A P G P L I V P Y N L
                                |                 |       |           |     |
L-MYC  105  E R L E R A V S D R L A P G A P R G N P P K A S A A P D C T P S L
```

Fig-12

```
                                      GGGC GGACAGCCAA CGAGCGGAAA    1
                                                                  +60
  1  ATGGCAGACA ATTTTCGCT  CCATGATGCG TTATCTGGGT CTGGAAACCC AAACCCTCAA
      M  A  D   N  F  S  L  H  D  A   L  S  G    S  G  N  P   Q
                                                                  +120
 21  GGATGGCCTG GCGCATGGGG GAACCAGCCT GCTGGGCAGG GGCTACCAGG GGCTTCCTAT
      G  W  P   G  A  W  G   N  Q  P   A  G  Q   G  L  P    G  A  S  Y
                                                                  +180
 41  CCTGGGGCCT ACCCGGGCCT ACCCCGGCAG CACCCCAGGC CAGCACCTCC AGGCGCTACC
      P  G  A   Y  P  G     L  P  R   Q  H  P    R  P  S    R  R  Y
                                       T  P      G  A  T
                                                                  +240
 61  ATGGAGCACG TGGAGCTTAT CCGGAGCACC TGCACCTGGA GTCTACGCAC CCAGCCTGGG
      M  E  H   V  E  L    I  R  S    T  C  T    W  S  L    R  T  Q  P  G
                                                                  +300
 81  GCCTACCCAT CTTCTGGACA GCCAAGTGCC CCCGGAGCCC ACCCTGCCAC TGCCCCTATG
      A  Y  P   S  S  G    Q  P  S    A  P  G    A  Y  P    A  T  A  P  M
                                                                  +360
101  GCGCCTGCTG GGCCACTGAT TGTGCCTTAT AACCTGCCTT TGCCTGGGGG AGTGGTGCCT
      A  P  A   G  P  L    I  V  P    Y  N  L    P  L  P    G  G  V  V  P
```

Fig–13A

```
     CGCATGCTGA TAACAATTCT GGGCACGGTG AAGCCCAATG CAAACAGAAT TGCTTTAGAT  +420
121    R  M  L    I  T  I    L  G  T  V    K  P  N    A  N  R  I    A  L  D

TTCCAAAGAG GGAATGATGT TGCCTTCCAC TTTAACCCAC GCTTCAATGA GAACAACAGG  +480
141    F  Q  R    G  N  D  V    A  F  H    F  N  P    R  F  N  E    N  N  R

AGAGTCATTG TTTGCAATAC AAAGCTCCAT AATAACTGGG GAAGGGAAGA AAGACAGTCG  +540
161    R  V  I    V  C  N  T    K  L  H    N  N  W    G  R  E  E    R  Q  S

GTTTTCCCAT TTGAAAGTGG GAAACCATTC AAAATACATG TACTGGTTGA ACCTGACCAC  +600
181    V  F  P    F  E  S  G    K  P  F    K  I  H    V  L  V  E    P  D  H

TTGAAGGTTG CAGTGAATGA TGCTCACTTG TTGCAGTACA ATCATCGGGT TAAAAAACTC  +660
201    L  K  V    A  V  N  D    A  H  L    L  Q  Y    N  H  R  V    K  K  L

AATGAAATCA GAAAACTGGG AATTTCTGGT GACATAGACC TCACCAGTGC TTCATATACC  +720
221    N  E  I    R  K  L  G    I  S  G    D  I  D    L  T  S  A    S  Y  T

ATGATATAAT CTGAAAGGGG CAGATTAAAA AAAAAAAAAA AGAATCTAAA CCTTACATGT  +780
241    M  I  *

GTAAAGGTTT CATGTTCACT GTGAGAGAAA ATTTTTACAT TCATCAATAT CCCCCCGCCC  +840
```

Fig-13B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 878 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: L-31-gal-lectin cDNA ( i x ) FEATURE:
        ( A ) NAME/KEY: CDS
        ( B ) LOCATION: 19..768

( x i ) SEQUENCE DESCRIPTION: SEQ ID NO:1:

```
GCAGCCACCG AGCGGAAA ATG GCA GAC AAT TTT TCG CTC CAT GAT GCG TTA        51
                    Met Ala Asp Asn Phe Ser Leu His Asp Ala Leu
                     1               5                      10

TCT GGG TCT GGA AAC CCA AAC CCT CAA GGA TGG CCT GGC GCA TGG GGG        99
Ser Gly Ser Gly Asn Pro Asn Pro Gln Gly Trp Pro Gly Ala Trp Gly
            15              20                  25

AAC CAG CCT GCT GGG GCA GGG GGC TAC CCA GGG GCT TCC TAT CCT GGG       147
Asn Gln Pro Ala Gly Ala Gly Gly Tyr Pro Gly Ala Ser Tyr Pro Gly
        30              35                  40
```

| | | | | | | | | | | | | | | | | |
|---|---|---|---|---|---|---|---|---|---|---|---|---|---|---|---|---|
| GCC | TAC | CCC | GGG | CAG | GCA | CCC | CCA | GGG | GCT | TAT | CCT | GGA | CAG | GCA | CCT | 195 |
| Ala | Tyr | Pro | Gly | Gln | Ala | Pro | Pro | Gly | Ala | Tyr | Pro | Gly | Gln | Ala | Pro | |
| | 45 | | | | 50 | | | | | 55 | | | | | | |
| CCA | GGC | GCC | TAC | CAT | GGA | GCA | CCT | GGA | GCT | TAT | CCC | GGA | GCA | CCT | GCA | 243 |
| Pro | Gly | Ala | Tyr | His | Gly | Ala | Pro | Gly | Ala | Tyr | Pro | Gly | Ala | Pro | Ala | |
| 60 | | | | | 65 | | | | | 70 | | | | | 75 | |
| CCT | GGA | GTC | TAC | CCA | GGG | CCA | CCC | AGC | GGC | CCT | GGG | GCC | TAC | CCA | TCT | 291 |
| Pro | Gly | Val | Tyr | Pro | Gly | Pro | Pro | Ser | Gly | Pro | Gly | Ala | Tyr | Pro | Ser | |
| | | | | 80 | | | | | 85 | | | | | 90 | | |
| TCT | GGA | CAG | CCA | AGT | GCC | CCC | GGA | GCC | TAC | CCT | GCC | ACT | GGC | CCC | TAT | 339 |
| Ser | Gly | Gln | Pro | Ser | Ala | Pro | Gly | Ala | Tyr | Pro | Ala | Thr | Gly | Pro | Tyr | |
| | | | 95 | | | | | 100 | | | | | 105 | | | |
| GGC | GCC | CCT | GCT | GGG | CCA | CTG | ATT | GTG | CCT | TAT | AAC | CTG | CCT | TTG | CCT | 387 |
| Gly | Ala | Pro | Ala | Gly | Pro | Leu | Ile | Val | Pro | Tyr | Asn | Leu | Pro | Leu | Pro | |
| | | 110 | | | | | 115 | | | | | 120 | | | | |
| GGG | GGA | GTG | GTG | CCT | CGC | ATG | CTG | ATA | ACA | ATT | CTG | GGC | ACG | GTG | AAG | 435 |
| Gly | Gly | Val | Val | Pro | Arg | Met | Leu | Ile | Thr | Ile | Leu | Gly | Thr | Val | Lys | |
| | 125 | | | | | 130 | | | | | 135 | | | | | |
| CCC | AAT | GCA | AAC | AGA | ATT | GCT | TTA | GAT | TTC | CAA | AGA | GGG | AAT | GAT | GTT | 483 |
| Pro | Asn | Ala | Asn | Arg | Ile | Ala | Leu | Asp | Phe | Gln | Arg | Gly | Asn | Asp | Val | |
| 140 | | | | | 145 | | | | | 150 | | | | | 155 | |
| GCC | TTC | CAC | TTT | AAC | CCA | CGC | TTC | AAT | GAG | AAC | AAC | AGG | AGA | GTC | ATT | 531 |
| Ala | Phe | His | Phe | Asn | Pro | Arg | Phe | Asn | Glu | Asn | Asn | Arg | Arg | Val | Ile | |
| | | | | 160 | | | | | 165 | | | | | 170 | | |
| GTT | TGC | AAT | ACA | AAG | CTG | GAT | AAT | AAC | TGG | GGA | AGG | GAA | GAA | AGA | CAG | 579 |
| Val | Cys | Asn | Thr | Lys | Leu | Asp | Asn | Asn | Trp | Gly | Arg | Glu | Glu | Arg | Gln | |
| | | | 175 | | | | | 180 | | | | | 185 | | | |
| TCG | GTT | TTC | CCA | TTT | GAA | AGT | GGG | AAA | CCA | TTC | AAA | ATA | CAT | GTA | CTG | 627 |
| Ser | Val | Phe | Pro | Phe | Glu | Ser | Gly | Lys | Pro | Phe | Lys | Ile | His | Val | Leu | |
| | | 190 | | | | | 195 | | | | | 200 | | | | |
| GTT | GAA | CCT | GAC | CAC | TTC | AAG | GTT | GCA | GTG | AAT | GAT | GCT | CAC | TTG | TTG | 675 |
| Val | Glu | Pro | Asp | His | Phe | Lys | Val | Ala | Val | Asn | Asp | Ala | His | Leu | Leu | |
| | 205 | | | | | 210 | | | | | 215 | | | | | |
| CAG | TAC | AAT | CAT | CGG | GTT | AAA | AAA | CTC | AAT | GAA | ATC | AGA | AAA | CTG | GGA | 723 |
| Gln | Tyr | Asn | His | Arg | Val | Lys | Lys | Leu | Asn | Glu | Ile | Arg | Lys | Leu | Gly | |
| 220 | | | | | 225 | | | | | 230 | | | | | 235 | |
| ATT | TCT | GGT | GAC | ATA | GAC | CTC | ACC | AGT | GCT | TCA | TAT | ACC | ATG | ATA | | 768 |
| Ile | Ser | Gly | Asp | Ile | Asp | Leu | Thr | Ser | Ala | Ser | Tyr | Thr | Met | Ile | | |
| | | | 240 | | | | | 245 | | | | | 250 | | | |

| | |
|---|---|
| TAATCTGAAA GGGGCAGATT AAAAAAAAAA AAAAAGAATC TAAACCTTAC ATGTGTAAAG | 828 |
| GTTTCATGTT CACTGTGAGA GAAAATTTTT ACATTCATCA ATATCCCCCC | 878 |

( 2 ) INFORMATION FOR SEQ ID NO:2:

( i ) SEQUENCE CHARACTERISTICS:
        ( A ) LENGTH: 250 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Asp | Asn | Phe | Ser | Leu | His | Asp | Ala | Leu | Ser | Gly | Ser | Gly | Asn |
| 1 | | | | 5 | | | | | 10 | | | | | 15 | |
| Pro | Asn | Pro | Gln | Gly | Trp | Pro | Gly | Ala | Trp | Gly | Asn | Gln | Pro | Ala | Gly |
| | | | 20 | | | | | 25 | | | | | 30 | | |
| Ala | Gly | Gly | Tyr | Pro | Gly | Ala | Ser | Tyr | Pro | Gly | Ala | Tyr | Pro | Gly | Gln |
| | | 35 | | | | | 40 | | | | | 45 | | | |
| Ala | Pro | Pro | Gly | Ala | Tyr | Pro | Gly | Gln | Ala | Pro | Pro | Gly | Ala | Tyr | His |
| | 50 | | | | | 55 | | | | | 60 | | | | |

| Gly | Ala | Pro | Gly | Ala | Tyr | Pro | Gly | Ala | Pro | Ala | Pro | Gly | Val | Tyr | Pro |
| 65 | | | | 70 | | | | | 75 | | | | | | 80 |

| Gly | Pro | Pro | Ser | Gly | Pro | Gly | Ala | Tyr | Pro | Ser | Ser | Gly | Gln | Pro | Ser |
| | | | | 85 | | | | | 90 | | | | | 95 | |

| Ala | Pro | Gly | Ala | Tyr | Pro | Ala | Thr | Gly | Pro | Tyr | Gly | Ala | Pro | Ala | Gly |
| | | | 100 | | | | | 105 | | | | | 110 | | |

| Pro | Leu | Ile | Val | Pro | Tyr | Asn | Leu | Pro | Leu | Pro | Gly | Gly | Val | Val | Pro |
| | | 115 | | | | | 120 | | | | | 125 | | | |

| Arg | Met | Leu | Ile | Thr | Ile | Leu | Gly | Thr | Val | Lys | Pro | Asn | Ala | Asn | Arg |
| | 130 | | | | | 135 | | | | | 140 | | | | |

| Ile | Ala | Leu | Asp | Phe | Gln | Arg | Gly | Asn | Asp | Val | Ala | Phe | His | Phe | Asn |
| 145 | | | | | 150 | | | | | 155 | | | | | 160 |

| Pro | Arg | Phe | Asn | Glu | Asn | Asn | Arg | Arg | Val | Ile | Val | Cys | Asn | Thr | Lys |
| | | | | 165 | | | | | 170 | | | | | 175 | |

| Leu | Asp | Asn | Asn | Trp | Gly | Arg | Glu | Glu | Arg | Gln | Ser | Val | Phe | Pro | Phe |
| | | | 180 | | | | | 185 | | | | | 190 | | |

| Glu | Ser | Gly | Lys | Pro | Phe | Lys | Ile | His | Val | Leu | Val | Glu | Pro | Asp | His |
| | | | 195 | | | | 200 | | | | | 205 | | | |

| Phe | Lys | Val | Ala | Val | Asn | Asp | Ala | His | Leu | Leu | Gln | Tyr | Asn | His | Arg |
| | 210 | | | | | 215 | | | | | 220 | | | | |

| Val | Lys | Lys | Leu | Asn | Glu | Ile | Arg | Lys | Leu | Gly | Ile | Ser | Gly | Asp | Ile |
| 225 | | | | | 230 | | | | | 235 | | | | | 240 |

| Asp | Leu | Thr | Ser | Ala | Ser | Tyr | Thr | Met | Ile |
| | | | | 245 | | | | | 250 |

( 2 ) INFORMATION FOR SEQ ID NO:3:

( i ) SEQUENCE CHARACTERISTICS:
        ( A ) LENGTH: 916 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..792

( x i ) SEQUENCE DESCRIPTION: SEQ ID NO:3:

| ATG | GCA | GAC | ACG | TTT | TCG | CTT | AAC | GAT | GCC | TTA | GCT | GGC | TCT | GGA | AAC | 48 |
| Met | Ala | Asp | Thr | Phe | Ser | Leu | Asn | Asp | Ala | Leu | Ala | Gly | Ser | Gly | Asn | |
| 1 | | | | 5 | | | | | 10 | | | | | 15 | | |

| CCA | AAC | CCT | CAA | GGA | TAT | CCG | GGT | GCA | TGG | GGG | AAC | CAG | CCT | GGG | GCA | 96 |
| Pro | Asn | Pro | Gln | Gly | Tyr | Pro | Gly | Ala | Trp | Gly | Asn | Gln | Pro | Gly | Ala | |
| | | | | 20 | | | | | 25 | | | | | 30 | | |

| GGG | GGC | TAC | CCA | GGG | GCT | GCC | TAT | CCT | GGG | GCC | TAT | CCA | GGA | CAG | GCT | 144 |
| Gly | Gly | Tyr | Pro | Gly | Ala | Ala | Tyr | Pro | Gly | Ala | Tyr | Pro | Gly | Gln | Ala | |
| | | 35 | | | | | 40 | | | | | 45 | | | | |

| CCT | CCA | GGG | GCC | TAC | CCA | GGA | CAG | GCT | CCT | CCA | GGG | GCC | TAT | CCA | GGA | 192 |
| Pro | Pro | Gly | Ala | Tyr | Pro | Gly | Gln | Ala | Pro | Pro | Gly | Ala | Tyr | Pro | Gly | |
| | 50 | | | | | 55 | | | | | 60 | | | | | |

| CAG | GCT | CCT | CCT | AGT | GCC | TAC | CCC | GGC | CCA | ACT | GCC | CCT | GGA | GCT | TAT | 240 |
| Gln | Ala | Pro | Pro | Ser | Ala | Tyr | Pro | Gly | Pro | Thr | Ala | Pro | Gly | Ala | Tyr | |
| 65 | | | | | 70 | | | | | 75 | | | | | 80 | |

| CCT | GGC | CCA | ACT | GCC | CCT | GGA | GCT | TAT | CCT | GGC | TCA | ACT | GCC | CCT | GGA | 288 |
| Pro | Gly | Pro | Thr | Ala | Pro | Gly | Ala | Tyr | Pro | Gly | Ser | Thr | Ala | Pro | Gly | |
| | | | | 85 | | | | | 90 | | | | | 95 | | |

```
GCC  TTC  CCA  GGG  CAA  CCT  GGG  GCA  CCT  GGG  GCC  TAC  CCC  AGT  GCT  CCT          336
Ala  Phe  Pro  Gly  Gln  Pro  Gly  Ala  Pro  Gly  Ala  Tyr  Pro  Ser  Ala  Pro
               100                      105                      110

GGA  GGC  TAT  CCT  GCT  GCT  GGC  CCT  TAT  GGT  GTC  CCC  GCT  GGA  CCA  CTG          384
Gly  Gly  Tyr  Pro  Ala  Ala  Gly  Pro  Tyr  Gly  Val  Pro  Ala  Gly  Pro  Leu
               115                      120                      125

ACG  GTG  CCC  TAT  GAC  CTG  CCC  TTG  CCT  GGA  GGA  CTC  ATG  CCC  CGC  ATG          432
Thr  Val  Pro  Tyr  Asp  Leu  Pro  Leu  Pro  Gly  Gly  Leu  Met  Pro  Arg  Met
               130                      135                      140

CTG  ATC  ACA  ATC  ATG  GGC  ACA  GTG  AAA  CCC  AAC  GCA  AAC  AGG  ATT  GTT          480
Leu  Ile  Thr  Ile  Met  Gly  Thr  Val  Lys  Pro  Asn  Ala  Asn  Arg  Ile  Val
145                      150                      155                      160

CTA  GAT  TTC  AGG  AGA  GGG  AAT  GAT  GTT  GCC  TTC  CAC  TTT  AAC  CCC  CGC          528
Leu  Asp  Phe  Arg  Arg  Gly  Asn  Asp  Val  Ala  Phe  His  Phe  Asn  Pro  Arg
               165                      170                      175

TTC  AAT  GAG  AAC  AAC  AGA  AGA  GTC  ATT  GTG  TGT  AAC  ACG  AAG  CAG  GAC          576
Phe  Asn  Glu  Asn  Asn  Arg  Arg  Val  Ile  Val  Cys  Asn  Thr  Lys  Gln  Asp
               180                      185                      190

AAT  AAC  TGG  GGA  AAG  GAA  GAA  AGA  CAG  TCA  GCC  TTC  CCC  TTT  GAG  AGT          624
Asn  Asn  Trp  Gly  Lys  Glu  Glu  Arg  Gln  Ser  Ala  Phe  Pro  Phe  Glu  Ser
               195                      200                      205

GGA  AAA  CCA  TTC  AAA  ATA  CAA  GTC  CTG  GTT  GAA  GCT  GAC  CAC  TTC  AAG          672
Gly  Lys  Pro  Phe  Lys  Ile  Gln  Val  Leu  Val  Glu  Ala  Asp  His  Phe  Lys
     210                      215                      220

GTT  GCG  GTC  AAC  GAT  GCT  CAC  CTA  CTG  CAG  TAC  AAC  CAT  CGG  ATG  AAG          720
Val  Ala  Val  Asn  Asp  Ala  His  Leu  Leu  Gln  Tyr  Asn  His  Arg  Met  Lys
225                      230                      235                      240

AAC  CTC  CGG  GAA  ATC  AGC  CAA  CTG  GGG  ATC  AGT  GGT  GAC  ATA  ACC  CTC          768
Asn  Leu  Arg  Glu  Ile  Ser  Gln  Leu  Gly  Ile  Ser  Gly  Asp  Ile  Thr  Leu
               245                      250                      255

ACC  AGC  GCT  AAC  CAC  GCC  ATG  ATC  TAAGCCAGAA  GGGGCGGCAC  CGAAACCGGC             822
Thr  Ser  Ala  Asn  His  Ala  Met  Ile
               260

CCTGTGTGCC  TTAGGAGTGG  GAAACTTTGC  ATTTCTCTCT  CCTTATCCTT  CTTGTAAGAC             882

ATCCATTTAA  TAAAGTCTCA  TGCTGAGAGA  AAAG                                          916
```

( 2 ) INFORMATION FOR SEQ ID NO:4:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Asp  Thr  Phe  Ser  Leu  Asn  Asp  Ala  Leu  Ala  Gly  Ser  Gly  Asn
1                   5                        10                       15

Pro  Asn  Pro  Gln  Gly  Tyr  Pro  Gly  Ala  Trp  Gly  Asn  Gln  Pro  Gly  Ala
               20                       25                       30

Gly  Gly  Tyr  Pro  Gly  Ala  Ala  Tyr  Pro  Gly  Ala  Tyr  Pro  Gly  Gln  Ala
               35                       40                       45

Pro  Pro  Gly  Ala  Tyr  Pro  Gly  Gln  Ala  Pro  Pro  Gly  Ala  Tyr  Pro  Gly
     50                       55                       60

Gln  Ala  Pro  Pro  Ser  Ala  Tyr  Pro  Gly  Pro  Thr  Ala  Pro  Gly  Ala  Tyr
65                       70                       75                       80

Pro  Gly  Pro  Thr  Ala  Pro  Gly  Ala  Tyr  Pro  Gly  Ser  Thr  Ala  Pro  Gly
               85                       90                       95
```

-continued

| Ala | Phe | Pro | Gly 100 | Gln | Pro | Gly | Ala | Pro 105 | Gly | Ala | Tyr | Pro | Ser 110 | Ala | Pro |
| Gly | Gly | Tyr 115 | Pro | Ala | Ala | Gly | Pro 120 | Tyr | Gly | Val | Pro | Ala 125 | Gly | Pro | Leu |
| Thr | Val 130 | Pro | Tyr | Asp | Leu | Pro 135 | Leu | Pro | Gly | Gly | Leu 140 | Met | Pro | Arg | Met |
| Leu 145 | Ile | Thr | Ile | Met | Gly 150 | Thr | Val | Lys | Pro | Asn 155 | Ala | Asn | Arg | Ile | Val 160 |
| Leu | Asp | Phe | Arg | Arg 165 | Gly | Asn | Asp | Val | Ala 170 | Phe | His | Phe | Asn | Pro 175 | Arg |
| Phe | Asn | Glu | Asn 180 | Asn | Arg | Arg | Val | Ile 185 | Val | Cys | Asn | Thr | Lys 190 | Gln | Asp |
| Asn | Asn | Trp 195 | Gly | Lys | Glu | Glu | Arg 200 | Gln | Ser | Ala | Phe | Pro 205 | Phe | Glu | Ser |
| Gly | Lys 210 | Pro | Phe | Lys | Ile | Gln 215 | Val | Leu | Val | Glu | Ala 220 | Asp | His | Phe | Lys |
| Val 225 | Ala | Val | Asn | Asp | Ala 230 | His | Leu | Leu | Gln | Tyr 235 | Asn | His | Arg | Met | Lys 240 |
| Asn | Leu | Arg | Glu | Ile 245 | Ser | Gln | Leu | Gly | Ile 250 | Ser | Gly | Asp | Ile | Thr 255 | Leu |
| Thr | Ser | Ala | Asn 260 | His | Ala | Met | Ile | | | | | | | | |

GALACTOSIDE-BINDING-PROTEIN USEFUL IN THE DIAGNOSIS AND INHIBITION OF OF METASTASIS

This is continuation of Ser. No. 08/188,225, filed Jan. 26, 1994, now abandoned which is a continuation-in-part application of Ser. No. 07/681,242, filed Apr. 5, 1991, now abandoned, which was a continuation-in-part of Ser. No. 07/294,249, filed Jan. 6, 1989, now abandoned.

A portion of the work described herein was supported by National Cancer Institute Grant CA-46120.

FIELD OF THE INVENTION

The present invention relates generally to methods and compositions for detecting the presence of tumors and for inhibiting metastasis. More specifically, the present invention relates to galactoside-binding-proteins which are useful in the detection and inhibition of metastasis.

BACKGROUND OF THE INVENTION

A considerable amount of research has been done in the area of cell adhesion and its role in tumor formation. It has been determined that a number of mammalian cells express endogenous carbohydrate-binding proteins on their surfaces and that the cell membranes of certain tumor cells express endogenous galactose-specific lectins. There is also evidence that tumor cells metastasize in part is due to complex intercellular interactions involving adhesion and aggregation. It is now believed that a specific class of tumor cell surface proteins, endogenous lectins, are important in the mediation of metastasis.

By immobilizing monosaccharides, oligosaccharides, or glycoproteins in affinity columns, lectins have been isolated from tumor tissue extracts. Generally, a tissue extract in acetone or the like is prepared to isolate the protein component from the lipid component. The acetone is then evaporated, whereupon the residue is solublized in a buffered aqueous solution. This solution is then passed through an affinity column containing the immobilized carbohydrates or glycoproteins. A number of lectins have been isolated in this manner which selectively bind to galactosides. Galactoside-specific lectins which occur most often are those with apparent molecular weights of 14,000 and between 29,000–34,000.

A number of studies have indicated that surface lectins interact with cell-surface carbohydrates causing adjacent cells to adhere to one another. For example, it is known that chicken hepatocytes have a N-acetylgulcosamine-specific lectin which mediates adhesion to gels derivatized with the corresponding sugar, and that adhesion can be interrupted by anti-lectin antibodies. Similarly, rat hepatocytes adhere to polystyrene coated with desialylated ceruloplasmin due to the presence of endogenous asialoglycolprotein-binding lectin. Another example of adhesion to a substratum which is mediated by lectins was found in extra-embryonic endoderm cells of chick embryos. It was found that a galactoside-specific lectin was deposited by the cells on the substratum. In this instance, it was demonstrated that by pre-treating the cells with beta-galactosidase cell aggregation was prevented. Purified lectin was also noted to induce cell aggregation. Finally, it appears that lectin forms bridges directly between cell surface glycoconjugates.

A number of investigators have demonstrated endogenous lectins in both transformed and tumor cell-types such as rodent and human sarcomas, hepatomas, lung carcinomas, mammary carcinomas, squamous cell carcinomas, ovarian and testicular teratocarcinomas, T- and B-iuman-lymphoblastoid cells, hairy cell leukemia and chronic lymphocytic leukemia, Hodgkin's Disease cells, murine leukemia, pituitary tumor and numerous other epithelial tumors. Detection has been by agglutination activity, fluoresceinated neoglycoprotein binding, affinity chromatography and by immunoblotting techniques with anti-lectin antibodies. A broad apparent molecular weight range has been observed (13,000 to 140,000). However, the majority of cell lines studied demonstrated lectins having apparent molecular weights of 13,000–14,000 and 29,000–35,000.

As further evidence of the role of cell surface lectins in adhesion and aggregation, the inventor of the present invention determined with co-workers that asialofetuin glycopeptides have the capacity to inhibit not only homotypic aggregation of murine melanoma and fibrosarcoma cells, but also the adhesion of the cells to a substratum. Similarly, it was found that anti-lectin monoclonal antibodies inhibit asialofetuin-induced homotypic aggregation and attachment to a substratum.

In addition to the clear interplay of cell surface carbohydrates and adhesion, a number of studies have been conducted which demonstrate the importance of cell surface carbohydrates in metastasis. In one such study, B16 melanoma cells were treated with tunicamycin which inhibited N-glycosylation, and which decreased the ability of the cells to adhere to cultured endothelial cells and to form lung colonies following injection into syngeneic mice. Inhibiting N-linked oligosaccharides was also found to affect bloodbornearrest of lymphoma cells in the spleen. It was also found that by removing cell surface alpha galactosyl residues from fibrosarcoma cells, the capacity of the cells to adhere to basement membrane components was decreased. The adhesion of metastatic rat hepatocarcinoma cells to endothelial cell monolayers is also known to be inhibited by methyl alpha-D-mannopyranoside and N-acetyl-D-galactosamine. A number of tumor cells present endogenous lectins on their cell surfaces as do many normal cell types, for example platelets, lymphocytes, hepatocytes, and endothelial cells, which may provide binding sites for circulating tumor cells.

In one study, it was found that metastatic lymphoma cells ESb form rosettes with hepatocytes, whereas non-metastatic parental Eb cells do not form rosettes. Intercellular adhesion was decreased by treatment with beta-galctosidase and asialoorosomucoid. The adhesion of TA3 carcinoma cells to hepatocytes was similarly inhibited by treatment with N-acetyl-D-galactosamine, asialofetuin, and Thomsen-Friedenreich antigen. In the latter case, it was possible to block adhesion with antibodies against the hepatocyte asialoglycoprotein receptor. Finally, the binding of the tumor cells to liver macrophages can be inhibited by treatment with N-acetyl-D-galactosamine, D-galactose, and L-fucose. Other cells expressing galactoside-specific lectins are known in the literature. Importantly, the present inventor has observed that neoplastic transformation with concomitant expression of an additional gal-lectin of apparent molecular weight of 34,000 occurs upon oncogene tranfection of normal rat embryonal fibroblasts which otherwise express only (W) 14,500 lectin species.

It is also now clearly established that cell surface lectins are significantly involved in metastasis. The inventor of the present invention and co-workers were able to make a quantitative comparison of the surface expression of lectin by labeling the cells with anti-lectin monoclonal antibodies which were then detected with fluorescent antibody probe. In clones of murine melanomas, B-16, K-1735, and UV-2237 fibrocarcinoma, it was demonstrated that a correlation exists between the density of cell surface lectins and metastatic properties, with an increase in lectin density being observed on more metastatic cells. Among related tumor cell variants of the K-1735 melanoma, the UV-2237 fibrosarcoma and the A31-angiosarcoma, expression of gal-lectin with an apparent molecular weight of 34,000 is highest in those cells that exhibit the greatest metastic potential as observed from lung colonization studies.

The inventor of the present invention and co-workers have also explored the in vivo action of tumor cell surface lectins. Accordingly, metastatic cells (B16–F1 and UV-2237-IP#) were treated with anti-lectin monoclonal antibodies or anti-H-2 monoclonal antibodies. The cells were then injected intravenously into syngeneic mice. It was found that treatment with the anti-lectin antibodies reduced the formation of lung metastases.

In European Patent Application No. 203107 (PCT No. 8602651), International Publication No. WO86/02651, having a priority date of Oct. 23, 1984, to Cramer et al., the disclosure of which is incorporated herein by reference, specific carbohydrate-binding proteins (lectins) of mammalian tumor cells are disclosed. The aforementioned patent application further suggests the possibility of the use of these lectins to provide corresponding monoclonal antibodies and subfragments of these antibodies through the use of hybridoma cell lines. It is also disclosed that these antibodies can be labeled with a fluorescent or radioactive group for use in an assay for tumors. It is also disclosed in the aforementioned patent application that the invention is useful in clinical diagnosis and therapeutic treatment for the inhibition of metastastation in mammals. However, the novel polypeptides of the present invention are not disclosed. Therefore, it would be desirable to provide other techniques for detecting and inhibiting metastasis predicated on the surface cell expression of lectins. To this end, the present invention is directed.

In the parent application the nucleotide sequence for the cDNA which encodes the human beta-D-galactoside-binding protein L-31-gal-lectin and the calculated amino acid sequence for this polynucleotide contains minor errors due to errors in sequencing. This continuation-in-part application correctly sets forth the sequence in FIG. 6 of the drawings. The disclosure of the parent application (Ser. No. 681,242 filed Apr. 5, 1991) is incorporated herein by reference. The sequences submitted for L-31-gal-lectin in application Serial No. 681,242 are shown in FIG. 13.

SUMMARY OF THE INVENTION

In accordance with the present invention, there is provided in one embodiment a polypeptide product having part or all of the primary structural conformation and biological properties of a naturally-occurring galactoside-binding-protein expressed on the cell surface of a mammalian tumor cell. More specifically, the present invention provides a substantially biologically pure volume of a specific beta-D-galactoside-binding polypeptide referred to herein as L-34-gal-lectin which is. expressed by fibrosarcoma cells of murine origin and fragments of this polypeptide and those polypeptides encoded by the allelic variants of the gene for this polypeptide and naturally occurring mutants thereof.

In another aspect, the present invention provides a substantially biologically pure volume of a polypeptide having all or a part of the primary structural conformation and biological properties of a naturally-occurring beta-D-galactoside-binding protein referred to herein as L-31-gal-lectin expressed by a class of human cells and fragments of this polypeptide and those polypeptides encoded by the allelic variants of the gene for this polypeptide and naturally occurring mutants thereof. More specifically, the present invention provides a human beta-D-galactoside-binding polypeptide which is expressed by human fibrosarcoma cells (HT-1080) and which has an apparent molecular weight of approximately 31,000.

The polypeptides of the present invention are produced as the product of prokaryotic or eukaryotic host expression of exogenous DNA sequences obtained by genomic, cDNA cloning, or by gene synthesis.

In still another aspect, the present invention provides recombinant polypeptides having at least 81% homology (as calculated by using standard procedures, such as the "Wisconsin Program" of the Genetics Computer Group) with either L-34-gal-lectin or L-31-gal-lectin.

In another aspect, the present invention provides monoclonal and polyclonal antibodies generated by standard means which are immunoreactive with the novel polypeptides and polypeptide fragments of the present invention and which are immunoreactive with naturally-occurring beta-D-galactoside-binding lectin as elucidated by the present invention.

Isolation and purification of microbially-expressed polypeptides as set forth by the present invention may be carried out by known means such as chromatographic separation or immunological separation. The present invention also provides cDNA sequences encoding the novel polypeptides of the present invention for expression by a host.

In another aspect, the present invention provides a method for detecting metastasis of mammalian cells which includes the steps of providing antibodies directed against the novel polypeptides of the present invention and which cross-react to the naturally-occurring beta-D-galactoside-binding lectin expressed on the surface of specific tumor cells; contacting the mammalian cells to be assayed with the novel antibodies; washing the cells to remove any unbound antibodies; labeling the attached novel antibodies; detecting and quantifying the labeled antibodies; and comparing the level of binding sites on the suspect cells to a known non-metastatic control. In another aspect, the present invention provides a method for assaying a cell sample for determining the probability of metastasis, which includes the steps of (1) contacting a cell sample to be tested for metastatic potential with a probe having a detectable label, wherein said probe is an antibody against a polypeptide having an amino acid sequence which is preferably at least 81% and more preferably at least 86% homologous with the amino acid sequence set forth in FIG. 6A and 6B (sequence ID No. 1), wherein said antibody is made by immunization techniques using said polypeptide; (2) removing excess probe from the cell sample; and (3) detecting the level of the probe bound to the cell sample to determine the level of expression of L-31-gal-lectin expressed by said cell sample, wherein the metastatic potential increases as the level of expression increases.

In another aspect, inhibition of metastasis is carried out by injecting an effective amount of the novel polypeptides of the present invention or fragments thereof having a length of greater than four consecutive amino acids into a mammalian subject in a quantity sufficient to suppress substantially all of the receptors for the corresponding galactoside-binding lectin on selective tumor cell surfaces. The length and identity of the fragment is sufficient to provide a 81% decrease in metastasis over controls as set forth in Example 3 below and as determined in accordance with the protocol set forth herein.

In still another aspect, the present invention comprises a recombinant DNA cloning vehicle comprising cDNA coding for either of the inventive polypeptides illustrated in the drawings.

In another aspect, the present invention provides a method for inhibiting metastasis of mammalian tumor cells which comprises the steps of injecting into a mammalian subject an effective amount of antibodies against the novel polypeptide Of the present invention which cross-react to the corresponding naturally-occurring beta-D-galactoside-binding lectin, the quantity injected being sufficient to bind substantially all of the beta-D-galactoside-binding lectins expressed on the surfaces of preselected tumor cells in the mammalian subject such that metastasis of these cells is inhibited.

Also comprehended by the invention are pharmaceutical compositions comprising effective amounts of the polypeptide products of the invention together with suitable diluents, adjuvants and/or carriers for inhibiting metastasis in mammalian subjects.

Numerous feature and advantages of the invention will become apparent to those skilled in the art based upon the following description of the preferred embodiments of the invention and the drawings in which:

BRIEF DESCRIPTION OF THE DRAWINGS

FIGS. 2A and 2B (sequence ID No. 3) illustrates the nucleotide sequence and deduced amino acid sequence of the L-34-gal-lectin. Nucleotides are numbered positively in the 5' to 3' direction beginning with the initiator methionine and are numbered negatively in the 3' to 5' direction in the 5' untranslated region (right). The predicted amino acid sequence in shown below the nucleotide sequence in one-letter amino code (left).

FIGS. 6A and 6B (sequence ID No. 1) depicts the complete nucleotide and predicted protein sequence of the human beta-D-galactoside-binding protein L-31-gal-lectin. Nucleotides are numbered positively in the 5'-3' direction, beginning with the initiator methionine and are numbered negatively in the 3'-5' direction in the 5'-untranslated region (right). The predicted amino acid sequence is shown below the nucleotide sequence in one-letter amino acids (left).

FIG. 7 illustrates homology between the mouse (L-M) and the human (H-L) galactoside-binding proteins using the following symbols: vertical lines, identical residues; ●, conserved amino acid substitution; numbers, position of amino acids from the first methionine; and . . . , gaps added for optimal alignment.

FIGS. 8, 9, and 10 illustrate alignment of L-31-gal-lectin with L-34-gal-lectin and 6 Mr 14,000 galactoside-binding proteins using the following symbols: numbers, position from the first methionine; boxes, enclose residues homologous between L-31-gal-lectin polypeptide and the others; -, missing residue; and Δ, unique substitution found only in the two larger molecular weight proteins. Sequences were obtained from the following references. which are incorporated herein by reference:

Paroutaud, P., et al. Proc. Natl. Acad. Sci., USA, 82:6345–6348, 1987.

Hirabayshi, et al. J. Biochem., 101:775–787, 1987.

Southan, C., et al. FEBS Lett., 215:301–304, 1987.

Abbot, W. M., and Feizi, T., J. Biochem., 259:291–296, 1989.

Hirabayashi, J., and Kasai, K. I., J. Biochem., 109:1–6, 1988.

Merkle, R. K. et al. Arch. Biochem. Biophys., 274:404–416, 1989.

Raz, A., et al. Cancer Res., 48:645-649, 1988.

Figure 11:
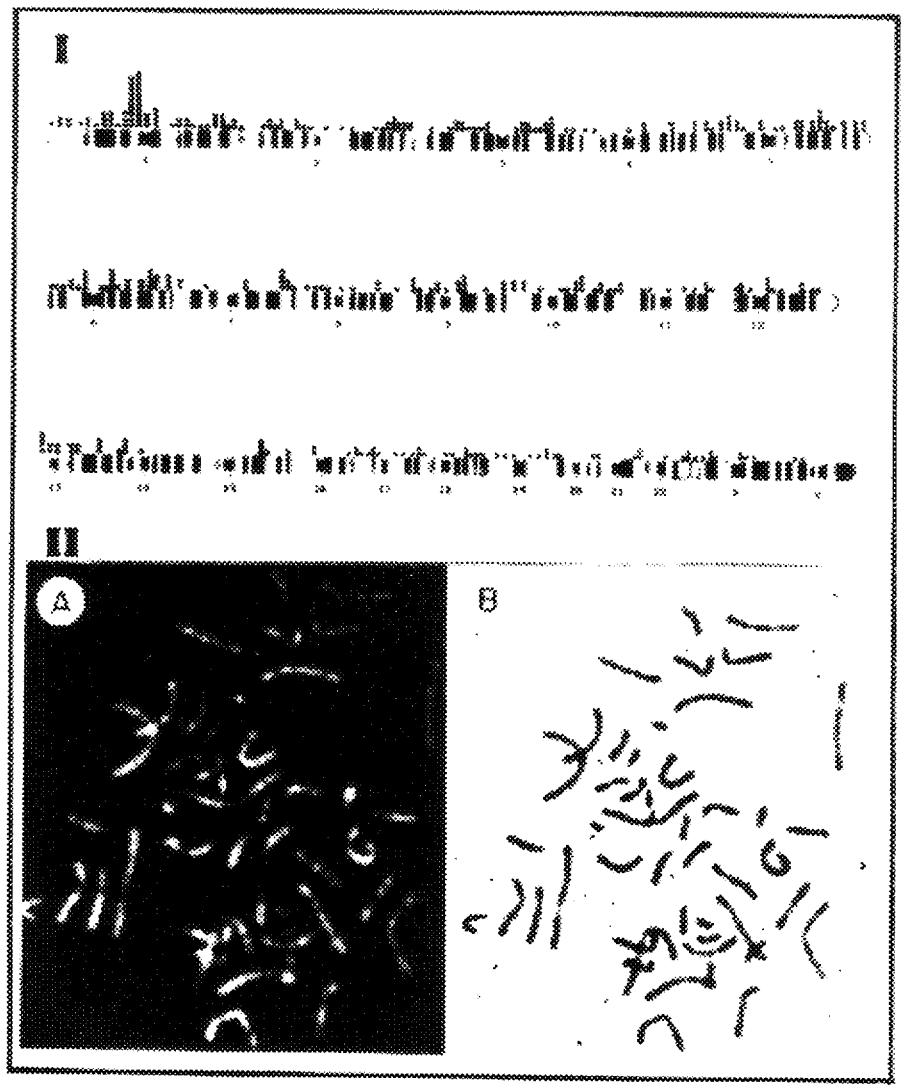

FIGS. 11-I, 11-IIA, and 11-IIB depict in situ hybridization of the human beta-D-galactoside-binding protein cDNA clone to normal metaphase chromosomes as follows: (11-I) ideograms of human chromosomes ● silver grain; (11-IIA) metaphase spread (cells were stained with quinacrine dihydrochloride and photographed for chromosome identification prior to hybridization); (11-IIB) autoradiograph after in situ hybridization of the chromosomal spread shown in (11-IIA).

FIG. 12 illustrates the homology between the amino terminal domain of human beta-D-galactoside-binding lectin and exon 2 domain of L-myc using the following symbols: boxes, enclose identical residues; ●, conserved amino acid substitution (Bestfit Program, University of Wisconsin Genetics Computer Group); numbers, position of amino acid from the first methionine; and -, gaps added for optimal alignment.

FIGS. 13A and 13B depict the incorrect sequence of L-31-gal-lectin of the parent application Ser. No. 681,242 as originally sequenced.

DETAILED DESCRIPTION OF THE PREFERRED EMBODIMENTS

In accordance with the present invention, DNA sequences encoding part or all of the polypeptide sequence of a specific beta-D-galactoside-binding lectin expressed by the cell membrane of UV-2237-IP3 murine fibrosarcoma cells and UV-2240 murine fibrosarcoma cells have been isolated and characterized. The murine-derived DNA coding for this polypeptide sequence has been expressed in a prokaryotic host to provide quantities of polypeptides having substantial biological similarity to the naturally-occurring beta-D-galactoside-binding lectin of the aforementioned murine fibrosarcomas and having an apparent molecular weight of approximately 34,000.

The DNA of murine origin was isolated from a genomic DNA library. Accordingly, murine UV-2237-IP3 fibrosarcoma cells (ultraviolate-induced fibrosarcomas) were grown as a monolayer on plastic in Dulbecco's modified Eagle's medium (GIBCO) containing 10% heat-inactivated fetal bovine serum, nonessential amino acids, and antibiotics. The cells were maintained at 37 degrees C. in a humidified atmosphere of 7% $CO_2$-93% air. Cytoplasmic RNA was extracted and the poly (A)$^+$-containing RNA was separated and enriched by two cycles of chromatography on oligo(dT)-cellulose columns. A cDNA clone library was constructed in the phage expression vector lambda-gt11. Techniques for constructing transformation vectors and the transformation of unicellular host organisms are well known, such as those set forth in U.S. Pat. No. 4,237,224 to Cohen et al., which is incorporated herein.

Double-stranded DNA complementary to the polyadenylated fibrosarcoma cell RNA (5 micrograms) was prepared using the RNAase H, utilizing a cDNA synthesis kit (Amersham). Following phenol extraction and ethanol precipitation, the fragments were methylated at the EcoRI sites, ligated (T4 ligase) to phosphorylated EcoRI linkers (Biolabs), and digested with EcoRI restriction enzyme (Pharmacia). The cDNA was sized by electrophoresis in 1% agarose gels using lambda-DNA digested with HindIII and pBR HinfI cuts as size markers. Fragments of 200–600 bp (LcDNA) and of 600–2000 bp (McDNA) were cut out, electroeluted, and passed through an Elutip-d-Column (Scheicher Schuell). LcDNA (350 ng) and McDNA (225 ng) were ligated to 3.5 micrograms and 1.75 micrograms of EcoRI-restricted dephosphorylated lambda-gt11 arms (Protoclone Kit, Promega), respectively. The ligated DNAs were picked in vitro, using the Amersham packaging kit. The primary libraries that contained $2.8 \times 10^5$ (LcDNA) and $1.8 \times 10^5$ (McDNA) independent recombinants were screened without further amplification. The libraries were screened at a density of 15000 plaque-forming units (PFU) per 150 mm plate. After 3 h at 42 degrees C., the plates were transferred to 37 degrees C. and nitrocellulose filters presaturated with 10 mM IPTG (isopropyl-D-thiogalactopyranoside) were overlaid on the agar for 16 h. After washing with TBS buffer (150 mM CaCl, 50 mM Tris-Hcl, pH 8, containing 10% low-fat milk and 0.05% sodium azide), the filters were incubated with rabbit anti-lectin antibodies, preabsorbed with lysate Escherichia coli strain Y1090 bound in nitrocellulose and diluted 1:250 in TBS buffer for 2 h at 24 degrees C. Following washing in TBS buffer containing 0.02% Tween 20, the filters were reincubated with [$^{125}$I] protein A for 30 min at 24 degrees C($8 \times 10^6$ cpm/filter) and washed extensively, as above. Those plaques containing bacteriophages that generated positive signals were processed through successive rounds of antibody screening until 100% positive plaques were obtained. Another cDNA library was contracted from poly(A$^+$)-containing RNA of UV2240 murine UV-induced fibrosarcoma grown as above in lambda-gt-10 vector. The cDNA library was screened using $^{32}$P-labeled nick translated synthetic oligonucleotide primer (TTTTGCTTAACCATGCCTTA) as probe. The three subclones have identical restriction patterns in the overlapping region and hybridize with the same size mRNA of UV-2237 fibrosarcoma cells.

Selected positive clones were subjected to nucleotide sequence analysis to determine the polypeptide sequence of the specific beta-D-galactoside-binding lectin of the present invention. The nucleotide sequence and deduced amino acide sequence of the specific beta-D-galactoside binding lectin, which will be referred to hereinafter as "L-34-gal-lectin," having an apparent molecular weight of approximately 34,000 daltons, is shown in FIG. 2 of the drawings. L-34-gal-lectin is a functional tumor marker for a number of mammalian tumors.

FIGS. 2A and 2B (sequence ID No. 3) gives the complete sequence of 144 5'-flanking, 792 coding and 205 3'-flanking nucleotides. The 5'-nontranslated sequence is G+ C rich (87%) and the consensus initiation sequence (GGAG$_G{}^A$GNNATGG) surrounds the (ATG+1) codon. The open reading frame encodes 264 amino acids. Homology search leads to the finding that the 172–209 region shares a conserved sequence homology with other low-molecular weight gal-lectin of the vertebrate gal-lectin of an apparent molecular weight of 14,000 daltons. It is anticipated that this sequence will be particularly useful in the practice of the present invention. It should be noted that the predicted molecular weight of L-34-gal-lectin is 20,255 and that this predicted molecular weight is slightly less than the apparent molecular weight of 34,000. This is believed to be due to the predicted secondary structure of L-34-gal-lectin which includes two distinct half-domains of 136 and 128 amino acids for the amino and the carboxy-terminals, respectively. The amino-terminal half is composed of eight similar repeats of nine amino acids containing G-X-Y sequences characteristic of the collagen supergene family, and the carboxy half contains a globular structure which encompasses the putative vertebrate galactoside-binding lectin domain. The primary structures of three additional murine molecules of similar structure and sequence have been elucidated recently; the low affinity rat IgE-binding receptor, the fibroblast CBP35, and the Mac-2 antigen which is the major nonintegrin laminin-binding protein of macrophages. Like several other carbohydrate-binding proteins, these GBPs from different cell lineages may fulfill several biological activities, suggesting multifunctional domains in the molecule.

The N-terminal half of the protein contains predominantly beta-sheet type structures of neutral hydropathy domains, except for the origin of the NH2-region (1–12 amino acid residues). The C-terminal half is composed of alternating reverse turns and includes both hydrophobic and hydrophilic domains indicative of globular polypeptides. These structural arrangements could slow the migration of L-34-gal-lectin in SDS gels, leading to the observed size. Also, it should be noted that no glycosylation or phosphorylation sites were detected in the sequence.

It is believed that the galactoside binding domain of L-34-gal-lectin comprises amino acid residues 172–209 with reference to FIGS. 2A and 2B (sequence ID No. 3) of the drawings. It is also believedi that it is the C-terminus which is presented on the tumor cell surface.

As shown in FIG. 2, the nucleotide sequence and deduced amino acid sequence of the L-34-gal-lectin of murine origin and of the novel polypeptide effective in the diagnosis and inhibition of metastasis of mammalian tumor cells in accordance with the present invention is shown with the nucleotides numbered in the 5' to 3+ direction, beginning with the initiator methionine. The nucleotides are numbered negatively in the 3' to 5' direction in the 5'-untranslated region. The predicted amino acid sequence is shown below the nucleotide sequence in one-letter amino acid code.

In accordance with the present invention there is also provided a polypeptde and DNA sequences encoding all or a part of the polypeptide sequence of a specific beta-D-galactoside-binding lectin expressed by the cell membrane of human HT-1080 fibrosarcoma cells. The DNA coding for this polypeptide sequence has been expressed in a prokaryotic host to provide quantities of polypetides having substantial biological similarity to the naturally-occurring human galactoside lectin of the aforementioned human fibrsarcomas. These polypeptides have an apparent molecular weight of about 31,000.

The DNA of human origin was cloned from the human HT-1080 fibrosarcoma complementary DNA library. A partial complementary DNA clone containing the complete coding region was characterized and the deduced sequence encodes e polypeptide of 242 amino acids with the characteristics of a carbohydrate-binding protein. The gene coding for the human beta-D-galactoside-binding protein was mapped to the chromosomal band 1p13. The deduced amino acid sequence of the human beta-D-galactoside-binding protein revealed 95 residues at the amino terminus, homologous to the predicted amino acid sequence of the second exon of the human L-myc gene.

The DNA of human origin was isolated from a genomic DNA library. Accordingly the mouse L-34 cDNA clone, pM1 (as described in Raz et al, "Identification of the Metastasis-Associated Galactoside-binding lectin as a Chimeric Gene Product," Cancer Research 49: 3489-3493; 1989), was 5' end-labeled with [$\gamma$-$^{32}$P]ATP and used as a probe to screen $1.6 \times 10^6$ $\lambda$gt11 recombinant phages from a human HT-1080 fibrosarcoma cDNA library (Clontech). Briefly, plaques were transferred to nitrocellulose and were prehybridized at 65° C. for 3 h in a solution containing 5×Denhardt's solution-6× SSC-0.1% SDS-0.1 M NaPO$_4$, pH7.0–150 µg/ml of denatured herring sperm DNA. Hybridizations were done overnight at 65° C. in a prehybridization solution containing $10^6$–$10^7$ cpm/ml of probe. Following hybridization, filters were washed once in 3× SSC-0.1% SDS for 30 min, once in 0.5× SSC-0.1% SDS for 30 min, and once in 0.1% SDS for 15 min. All washes were at 65° C. cDNA restriction fragments were subcloned into Bluescript-SK vector and the nucleotide sequence of the cDNA was determined in both strands, in opposite directions by the dideoxy chain termination method. The T7 DNA Polymerase Sequenase Version 2.0 System was used for sequencing according to the instructions of the manufacture (U.S. Biochemical Corp.).

For Northern blot analysis, ten µg of cytoplasmic RNA was fractionated by electrophoresis on 1% formaldehyde agarose gels and blotted onto nitrocellulose. The filters were probed with [$^{32}$P]dATP-and [$^{32}$P]dCTP-labeled nick-translated probe (specific activity, 2–5×$10^8$ cpm/pg; 3×$10^7$ cpm/filter). The filters were washed twice in 2× SSC-0.2% SDS for 30 min at room temperature and twice in 0.1× SSC-0.1% SDS for 30 min at 50° C., before autoradiography.

For in situ hybridization, cells in metaphase were stained with quinacrine dihydrochloride and photographed for chromosome identification prior to hybridization. Before hybridization, the slides were treated with ribonuclease (100 µg/ml) in 2× SSC for 1 h at 37° C., rinsed in 2× SSC, and dehydrated through a series of ethanols. Chromosomal DNA was denatured by immersion of the slides in 70% formamide-2+ SSC for 3 min at 70° C. and then the slides were transferred immediately into a cold ethanol series. A $^3$H-labeled human galactoside-binding protein cDNA probe was prepared by nick-translation, utilizing [$^3$H]dATP, [$^3$H]dCTP, and [$^3$H]dTTP. The specific activity of the labeled probe was 5×$10^7$ cpm/pg. The $^3$H-labeled probe was denatured for 5 min at 70° C. in 50% formamide-2× SSC containing 10% dextran sulfate and carrier DNA (salmon sperm DNA, 50 µg/ml) and cooled quickly. An aliquot of the probe (30 µl) (1×$10^6$ cpm/ml) was placed on each slide and a coverslip applied. After incubation for 20 h at 37° C. in a humidified chamber, the slides were washed in 50% formamide-2× SSC and then in a 2× SSC bath at 39° C. Autoradiography was performed with Ilford K-2 nuclear emulsion in gel form for 2–4.5 weeks at 4° C. The slides were then developed with D-19 for 5 min and fixed for 5 min, followed by staining with 5% Giemsa.

Figure 4:
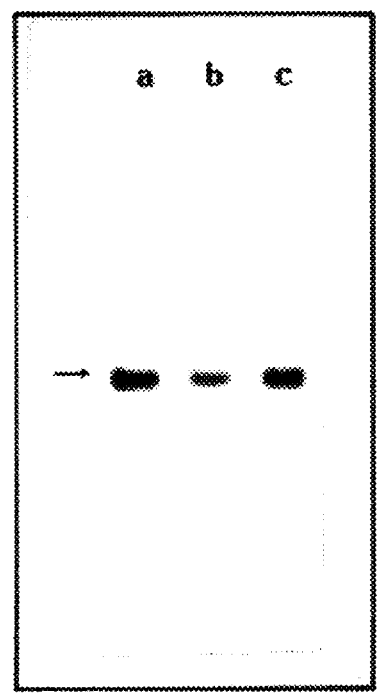
FIG. 4 depicts an immunoblot analysis of human tumor cell extracts by $(2\times10^5)$ polyclonal, monospecific antilectin antibodies to mouse L-34. (a) A375-melanoma; (b) HT-1080 fibrosarcoma; (c) Hela cervical carcinoma. (The arrow points to the migration of $M,31,000$.)

An immunoblot analysis was performed to establish the identity of the target antigen reactive with anti-mouse L-34 antibodies. As shown in FIG. 4, a monospecific polyclonal antibody raised in rabbits against a synthetic peptide from the mouse carboxy-terminal sequence domain recognizes a single immunoreactive polypeptide out of the total cell extract proteins from three human cell lines. This protein band migrates somewhat faster in SDS-PAGE [$M_r$ 31,000 (L-31)] than does the mouse L-34, which is consistent with the slight variations in migration observed among this family of proteins.

Figure 5:
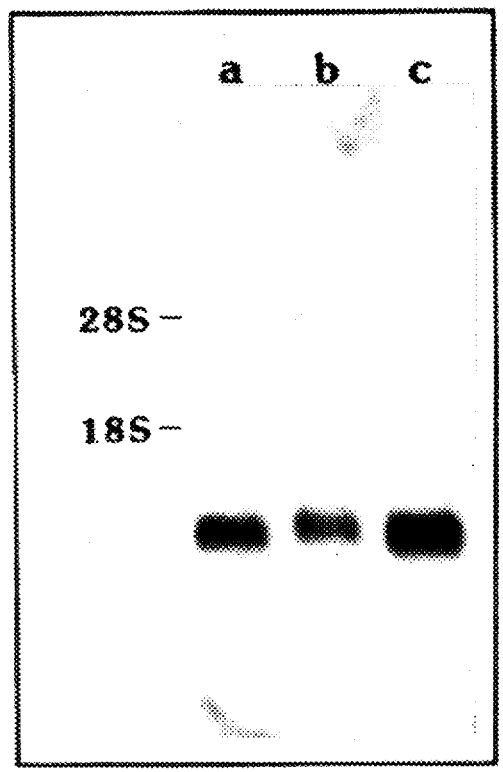
FIG. 5 depicts RNA blot hybridization of hL31 to 10 mg total RNA of (a) human Hela cervical carcinoma, (b) HT-1080 human fibrosarcoma, and (c) A375 human melanoma. (Positions of 18S and 28S rRNA are indicated.)

Screening of 1.6×106 $\lambda$gt11 recombinant phages from a human HT-1080 fibrosarcoma cDNA library (Clontech) resulted in the isolation of four hybridizing phage clones, each containing a single insert and hybridizing to the mouse pM1 clone. Restriction map analysis revealed that clone 3, the largest (~850 base pairs), shared a common restriction site (Sph1) with the mouse pM1 clone. The insert was designated hL31 and was utilized for subsequent studies. To determine the size and abundance of the L-31 mRNA, a Northern blot was performed with RNA extracted from three neoplastic human cell lines, using the hL31 clone as a probe. The three lanes in FIG. 5 show a single hybridizing band with a transcript size of about 1.2 kilobases.

FIGS. 6A and 6B (sequence ID No. 1) depicts the nucleotide sequence of the cDNA encoding L-31-gal-lectin, sequenced from both ends, and gives the sequence of 24 5'-flanking, 726 coding, and 111 3'-flanking nucleotides. The 5'-nontranslated sequence is G-plus-C-rich and the consensus initiation sequence surrounds the ATG(+1) codon (FIG. 7). An additional clone (clone 1) was sequenced in parallel and the two cDNA clones were found to be identical over the overlapping regions which encompass the first 391 base pairs of the 5' end. The discrepancy between the size of the isolated cDNA clone and that of the transcript estimated from the Northern analysis may be due to. a deficiency of 5' sequence, lack of polyadenylate tail, or both. The open reading frame encodes 242 amino acids, and the mature protein has a predicted molecular mass of 27,773 Da and is 22 amino acid residues shorter than the mouse L-34-gal-lectin homologue as shown in FIG. 7. This larger apparent size on SDS-PAGE (~$M_r$ 31,000) is likely secondary to the unique structure of this gene family which leads to an anomalous migration in SDS-PAGE. Alignment of the L-34-gal-lectin and L-31-gal-lectin as shown in FIG. 7, revealed deletion of two clusters of amino acids (72–79 and 95–108) in the L-31-gal-lectin amino-terminal half, as compared to L-34-gal-lectin, with an internal homology of 57.8% over 114 amino acids (FIG. 7). This partial loss of amino acid conservation together with the two 7 and 14 amino acid residue deletions have eliminated the eight internal repeats of 9 amino acids (YPGX$_{TP}$$^{AA}$PGA) found in the GBP murine gene family. The carboxy terminus of the L-31-gal-lectin polypeptide of the present invention shares a conserved sequence homology with the low molecular weight galactoside-lectin species ($M_r$ ~14,000) of other vertebrates and encompasses the putative galactoside-binding site, which is identical in size to that of L-34-gal-lectin (FIGS. 6–10). The degree of homology between L-31-gal-lectin and L-34-gal-lectin in the carboxy half-domain of the molecule is 85.9% over 128 amino acids (FIG. 7). The overall homology is 81.4% over the 242 amino acids of the entire protein. The hL31 hybridized in DNA-DNA binding, not only to the mL-34 but also the ML-14.5 lectin (not shown).

In situ hybridization experiments were performed with normal human metaphase chromosomes and hL31 as a probe. The predominant site of hybridization was the short arm of chromosome 1 with 17.3% of the total grain count (362 grains in 99 metaphases) (FIG. 5I). Forty-four percent of those grains were observed in the region 1p1centered on band 1p13 (FIG. 11A). The number of grains localized to this region represents at least 5-fold that of any other chromosomal region, suggesting that a single human galactoside-binding gene locus is present. Secondary sites of hybridization were found, presumably, because the galactoside-binding gene locus is present. Most likely, these secondary sites of hybridization were found because L-31-gal-lectin shares in part sequence homology with proteins containing G-X-Y sequences, especially at 2q, 6, 7q, and 13q which correspond to known loci of collagen genes, and the probe may have cross-hybridized with other GBP family members. Chromosomal aberrations in 1p13 are found in various neoplasias, i.e., malignant melanoma, adenocarcinoma of the breast and uterus, mesotheliomas, malignant lymphoma (B-ML, T-ML), and intestinal leiomyosarcoma.

A computer-assisted search of the National Biomedical Research Foundation protein data base using the FASTA program identified L-31-gal-lectin to be homologous with other GBPs, similarly to L-34-gal-lectin. The amino-terminal domain of the L-31-gal-lectin polypeptide was homologous with the second exon of the human gene product of L-myc. FIGS. 12 depicts a 31.5% identity over 95 amino acid residues; however, when the conserved amino acid substitutions are considered, the degree of homology increases to 70.5%. The homology of mL-31 to L-myc is insignificant (<20%) in this region.; The myc gene family includes c-, N-, and L-myc and probably other members as well. C-myc is expressed in most dividing cells and has been implicated in the development of many classes of tumors. N-myc has been found in a more restricted set of tumors most of which show neural characteristics, whereas L-myc amplification has so far been reported only in small cell lung carcinoma cells. Structural analysis within the myc gene family has demonstrated that each is composed of three exons and two introns and that they are developmentally regulated; their deregulated expression has been implicated in the development of tumors. A biochemical function of any of the members of the myc gene family is still speculative, although all members are known to code for nuclear phosphoproteins ($M_r$ 58,000–67,000). The human L-myc gene, unlike the other myc genes, expresses additional short-form polypeptides ($M_r$ 34,000 and 37,000) in small cell lung carcinoma cells. The short polypeptides are encoded predominantly by the second exon of the L-myc gene and are found in the cytoplasmic/membrane fraction. This molecular distribution is similar to the localization of GBPs. The function of this region in L-31-gal-lectin GBP and in the myc products is unknown. Previously, the amino terminus of the mouse-3T3 GBP, a known member of the CBP family, was found to be homologous (25%) to certain proteins of the heterogeneous nuclear ribonucleoprotein complex and was also localized in part to the nucleus. Taken together, those results imply a partially similar subcellular distribution between GBPs and several DNA- and RNA-binding proteins, including myc gene products. The myc family gene products share several other features with GBPs. Constitutively high expression of c-myc and L-34-gal-lectin is sufficient to confer anchorage independence upon normal fibroblasts. Elevated expression of both is thought to be involved in tumorigenicity and metastasis and both L-myc and hL31 map to the short arm of chromosome 1.

It has been established that low molecular weight polypeptides participate in immune reactions similar to the immune reactions of physiologically significant proteins. Most significantly, these low molecular weight polypeptides are known to provoke the formation of specific antibodies. The production of polyclonal and monoclonal antibodies using the novel polypeptides and fragments thereof (preferably greater than four amino acids in length) in the present invention by conventional antibody techniques will be apparent to those skilled in the art. Also, cultured growth of such transformed microbial hosts under conditions facilitative of large scale expression of the exogenous, vector-borne DNA sequences and isolation of the desired polypeptides of the present invention from the growth medium, cellular lysates or cellular membrane fractions will be understood by those skilled in the act. Similarly, having disclosed the amino acid sequence, methods for synthetically producing the polypeptides of the present invention will be known to those skilled in the art such as solid-phase polypeptide synthesis.

The following examples are presented by way of illustration of the invention and are not intended to in any way limit the scope of the present invention as reflected in the appended claims.

EXAMPLES

Example 1

Inhibition of Tumor Lung Colonization (Metastasis)

By a Synthetic Gal-Lectin Peptide

Cultured B16-F1melanoma and UV-2237-IP3 firbrosarcoma cultured cells were detached with 8 mMEDTA in $Ca^{++}$ and $Mg^{++}$-free phosphate buffered saline (pH 7.7) (CMF-PBS) and incubated on ice for 30 min with various concentrations of the novel synthetic polypeptide of the present invention having the amino acid sequence set forth in FIG. 2 of the drawings (Table 1).

Example 2

Preparation of Polyclonal Antibodies Against A Synthetic Gal-Lectin Peptide

Figure 1:
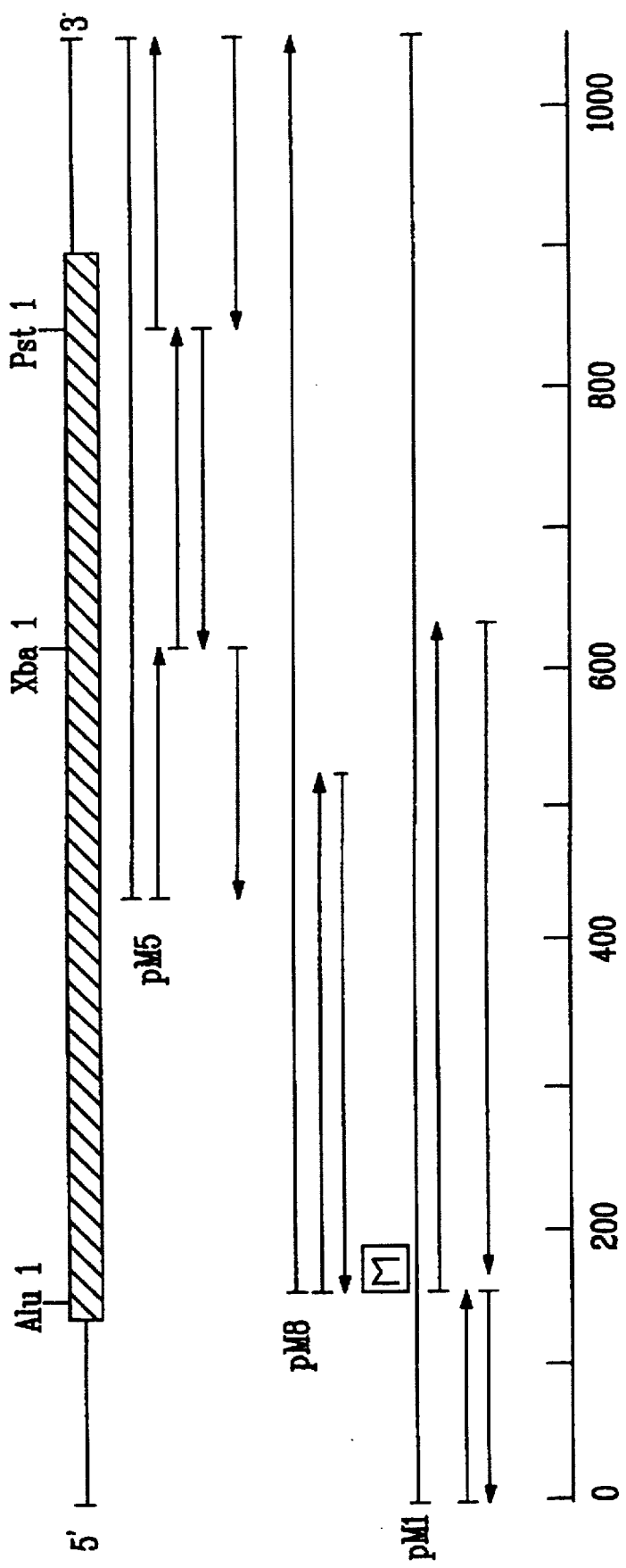
FIG. 1 is a partial restriction map and sequencing strategy for cDNA clones, pM5, pM8 and pM1 of the L-34-gal-lectin in accordance with the present invention. The map is drawn to scale showing the 5' to 3' orientation of the mRNA strand. The coding region for the novel polypeptide of the present invention containing 792 necleotides is shown as a hatched bar. Partial sequences hybridizing to the oligonucleotide probe are indicated.
Figure 3:
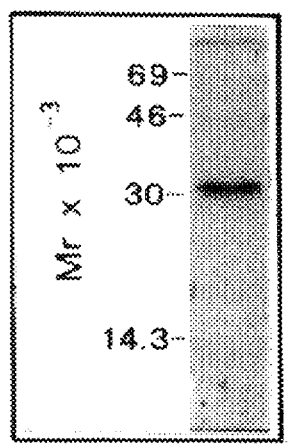
FIG. 3 is an immuioblot of UV-2237-IP3 fibrosarcoma cells and polyclonal anti-lectin antibodies. Numbers and bars at the left indicate the migration of $^{14}C$-labeled protein markers.

The synthetic polypeptide of Example 1 (approx. 35 micrograms) was mixed with complete Freund's adjuvant and injected near the popliteal lymph node of adult rabbit. Two additional boosts in incomplete Freund's adjuvant followed at two-week intervals and the rabbit was bled for antiserum preparation. Screening for the presence of specific anti-lectin antibodies in the serum was based on iumunoblotting of UV-2237-IP3 cell extracts. The immunoblot analysis is shown in FIG. 3.

The extract was then separated by 15% SDS-PAGE and transferred to a nitrocellulose filter. The nitrocellulose filter was incubated with mono-specific antibodies raised in a rabbit against a synthetic peptide of the 172–209 region of the L-34 lectin. After washing the filter, it was incubated with iodinated goat anti-rabbit IgG (ICN, 500,000 cPM/ml specific activity 11.4 Ci/micrograms). The filter was washed, dried, and autoradiographed. Numbers and bars at left indicate the migration of $^{14}C$-labeled protein markers.

Example 3

Inhibition of Tumor Lung Colonization (Metastasis By) Polyclonal antibodies to a Synthetic Gal-Lectin Peptide Female C57B1/6 mice (8 weeks old) were inoculated intravenously in the tail vein with $10^5$ B16-F1 melanoma cells treated. After 21 days, the mice were killed and autopsied, then their lungs were removed, rinsed, and fixed. The number of tumor colonies in the lungs were determined by counting under a dissecting microscope. In the experiments investigating the effect of antibody binding on lung colonizing ability of the cells, $1.5 \times 10^6$ cells were incubated for 30 min on ice in the presence of 1:1 diluted anti-lectin serum. The cells were then washed three times with cold CMF-PBS prior to the injection of $5 \times 10^4$ cells in 0.2 ml of CMF-PBS. Treatment in this manner produced a significant decrease in metastasis over controls as shown in Table 2 below.

Table 2

Inhibition of experimental lung metastasis by polyclonal antibodies against gal-lectin synthetic peptide. B16-F1 $10^5$ cells were injected intravenously. Cells were treated for 30 min at 4 degrees C. The non-absorbed antibodies were washed and the cells injected. Number of lung colonies per mouse:

| Control | 36,34,35,37,43,57,57 | 37 (26–57) |
|---|---|---|
| Antibody | 0,1,2,4,7,7,8,8,13 | 7 (0–13) |

(Two control animals died before the end of the experiment from excessive metastases. The size of the metastases was about three-fold larger in diameter then the treated group.)

Example 4

Determination of Metastatic Potential

A tissue sample from a mammalian subject would be prepared for in vitro analysis. Antibodies to L-34-gal-lectin or L-31-gal-lectin prepared in accordance with the present invention would be added to the tissue sample to bind either L-34-gal-lectin or L-31-gal-lectin expressed on the surfaces of the mammalian cells. Excess unbound antibodies would be removed. Anti-L-34-gal-lectin or anti-L-31-gal-lectin antibodies having a detectable marker such as a fluorescent label would be added to the cells. The fluorescent probes would bind to the bound L-34-gal-lectin or L-31-gal-lectin antibodies on the cell surfaces which could then be detectred in the conventional manner. The level of surface expression of L-34-gal-lectin or L-31-gal-lectin is indicative of the metastatic potential of the suspect cells.

While a particular embodiment of this invention is shown and described herein, it will be understood, of course, that the invention is not to be limited thereto since many modifications may be made, particularly by those skilled in this art, in light of this disclosure. It is contemplated therefore by the appended claims to cover any such modifications that fall within the true spirit and scope of this invention. For example, it is anticipated that fragments of novel polypeptides of the present invention greater than four amino acids in length will be suitable for diagnosing and inhibiting metastasis in accordance with the present invention.

The content of the paper sequence listing and the computer readable copies are the same.

What is claimed is:

1. A method of assaying a cell sample for determining the probability of metastasis, comprising the steps of:

contacting a cell sample to be tested for metastatic potential with a probe having a detectable label, wherein said probe is an antibody against a polypeptide having an amino acid sequence which is at least 86% homologous with the amino acid sequence set forth in FIGS. 6A and 6B (sequence ID No. 1), and wherein said antibody is directed against a portion of said polypeptide which is substantially homologous with said amino acid sequence, wherein said antibody binds to endogenous L-31-gal-lectin on a cell surface, wherein said antibody is made by immunization techniques using said polypeptide;

removing excess probe from said cell sample; and detecting the level of said probe bound to said cell sample to determine the level of expression of L-31-gal-lectin expressed by said cell sample, wherein said metastatic potential increases as said level of expression increases.

* * * * *